(12) United States Patent
Cai et al.

(10) Patent No.: US 9,939,401 B2
(45) Date of Patent: Apr. 10, 2018

(54) TEST SENSOR WITH MULTIPLE SAMPLING ROUTES

(71) Applicants: Xiaohua Cai, Changsha (CN); Hongli Che, Changsha (CN); Shaobo Li, Changsha (CN)

(72) Inventors: Xiaohua Cai, Changsha (CN); Hongli Che, Changsha (CN); Shaobo Li, Changsha (CN)

(73) Assignee: Changsha Sinocare Inc., Changsha, Hunan (CN)

( * ) Notice: Subject to any disclaimer, the term of this patent is extended or adjusted under 35 U.S.C. 154(b) by 445 days.

(21) Appl. No.: 14/184,764

(22) Filed: Feb. 20, 2014

(65) Prior Publication Data

US 2015/0233861 A1    Aug. 20, 2015

(51) Int. Cl.
*G01N 27/327* (2006.01)
*B01L 3/00* (2006.01)

(52) U.S. Cl.
CPC .............. *G01N 27/3272* (2013.01)

(58) Field of Classification Search
USPC ...................... 204/403.01–403.15
See application file for complete search history.

(56) References Cited

U.S. PATENT DOCUMENTS

| | | |
|---|---|---|
| 4,431,507 A | 2/1984 | Nankai et al. |
| 4,498,968 A | 2/1985 | Yamada et al. |
| 4,534,356 A | 8/1985 | Papadakis |
| 5,102,525 A | 4/1992 | Miyahara et al. |
| 5,120,420 A | 6/1992 | Nankai et al. |
| 5,126,034 A | 6/1992 | Carter et al. |
| 5,128,012 A | 7/1992 | Szuminsky et al. |
| 5,128,015 A | 7/1992 | Szuminsky et al. |
| 5,138,521 A | 8/1992 | Koshishi |

(Continued)

FOREIGN PATENT DOCUMENTS

| | | |
|---|---|---|
| CN | 94205849.6 | 6/1996 |
| CN | 99249332.3 | 8/2000 |

(Continued)

OTHER PUBLICATIONS

USPTO Office Action—U.S. Appl. No. 13/890,303, dated Oct. 20, 2015.

(Continued)

*Primary Examiner* — Jill A Warden
*Assistant Examiner* — Julie L Tavares
(74) *Attorney, Agent, or Firm* — Lambert & Associates; Gary E. Lambert; David J. Connaughton, Jr.

(57) ABSTRACT

An improved disposable electrochemical test sensor designed to facilitate sampling of fluid samples. It has a fluid chamber having a novel extra wide sampling entrance. The chamber provides a reservoir from which a sample fluid can be drawn into the chamber through capillary action. The novel extra wide sampling entrance of the test sensor provided by the present invention can draw blood into the chamber not only from the front of the sampling entrance as usual in convenient sensors, but also from the top, bottom, left corner and right corner of the sampling entrance. Thus it allows easy targeting the samples with small volume, picking up smeared samples and it is more tolerant to users who jam the tip of the sensor into users' finger.

15 Claims, 10 Drawing Sheets

(56) References Cited

U.S. PATENT DOCUMENTS

| | | |
|---|---|---|
| 5,264,103 A | 11/1993 | Yoshioka et al. |
| 5,344,545 A | 9/1994 | Tsukada et al. |
| 5,437,999 A | 8/1995 | Diebold et al. |
| 5,575,895 A | 11/1996 | Ikeda et al. |
| 5,582,697 A | 12/1996 | Ikeda et al. |
| 5,665,222 A | 9/1997 | Heller et al. |
| 5,708,247 A | 1/1998 | McAleer et al. |
| 5,739,039 A | 4/1998 | Hugues |
| 5,762,770 A | 6/1998 | Pritchard et al. |
| 5,858,201 A | 1/1999 | Otsuka et al. |
| 5,975,153 A | 11/1999 | Hill et al. |
| 6,004,441 A | 12/1999 | Fujiwara et al. |
| 6,071,391 A | 6/2000 | Gotoh et al. |
| 6,125,292 A | 9/2000 | Uenoyama et al. |
| 6,287,451 B1 | 9/2001 | Winarta et al. |
| 6,428,664 B1 | 8/2002 | Bhullar et al. |
| 6,540,891 B1 | 4/2003 | Stewart et al. |
| 6,592,746 B1 | 7/2003 | Feldman et al. |
| 6,645,359 B1 | 11/2003 | Bhullar et al. |
| 6,767,440 B1 | 7/2004 | Bhullar et al. |
| 6,767,441 B1 | 7/2004 | Cai et al. |
| 6,787,013 B2 | 9/2004 | Chang et al. |
| 6,793,802 B2 | 9/2004 | Lee et al. |
| 6,803,205 B2 | 10/2004 | Duffy et al. |
| 6,923,894 B2 | 8/2005 | Huang et al. |
| 6,942,770 B2 | 9/2005 | Cai et al. |
| 7,063,776 B2 | 6/2006 | Huang |
| 7,073,246 B2 | 7/2006 | Bhullar et al. |
| 7,118,667 B2 | 10/2006 | Lee |
| 7,276,146 B2 | 10/2007 | Wilsey |
| 7,288,174 B2 | 10/2007 | Cui et al. |
| 7,297,248 B2 | 11/2007 | Bae et al. |
| 7,386,937 B2 | 6/2008 | Bhullar et al. |
| 7,547,383 B2 | 6/2009 | Cai et al. |
| 7,641,785 B2 | 1/2010 | Shinno et al. |
| RE41,264 E | 4/2010 | Cai et al. |
| 7,740,746 B2 | 6/2010 | Huang |
| 7,802,467 B2 | 9/2010 | Wang |
| 7,824,616 B2 | 11/2010 | Katsuki et al. |
| 7,955,484 B2 | 6/2011 | Cai et al. |
| 7,967,962 B2 | 6/2011 | Wang et al. |
| RE42,567 E | 7/2011 | Hodges et al. |
| RE42,953 E | 11/2011 | Crismore et al. |
| 8,071,030 B2 | 12/2011 | Bhular et al. |
| 8,088,271 B2 | 1/2012 | Fujiwara et al. |
| 8,128,981 B2 | 3/2012 | Popovich et al. |
| 8,142,629 B2 | 3/2012 | Miyazaki et al. |
| 8,211,379 B2 | 7/2012 | Burke et al. |
| 8,222,044 B2 | 7/2012 | Bhullar et al. |
| 8,287,703 B2 | 10/2012 | Bhullar et al. |
| RE43,815 E | 11/2012 | Crismore et al. |
| 8,303,801 B2 | 11/2012 | Wilsey |
| 8,241,486 B2 | 12/2012 | Petyt et al. |
| 8,323,464 B2 | 12/2012 | Pugh et al. |
| 8,377,378 B2 | 2/2013 | Feldman et al. |
| 8,414,761 B2 | 4/2013 | Gotoh et al. |
| 8,414,762 B2 | 4/2013 | Petyt et al. |
| 8,430,999 B2 | 4/2013 | Onoda et al. |
| 8,480,869 B2 | 7/2013 | Fujiwara et al. |
| 8,506,775 B2 | 8/2013 | Surridge et al. |
| 8,511,147 B2 | 9/2013 | Wang |
| 8,535,497 B2 | 9/2013 | Fujiwara et al. |
| 8,540,864 B2 | 9/2013 | Fujiwara et al. |
| 8,551,308 B2 | 10/2013 | Bhullar et al. |
| 8,679,309 B2 | 3/2014 | Beer et al. |
| 2001/0034068 A1 | 10/2001 | Spivey et al. |
| 2004/0050717 A1 | 3/2004 | Teodorczyk et al. |
| 2005/0019212 A1* | 1/2005 | Bhullar ............ G01N 27/3272 422/400 |
| 2005/0145490 A1 | 7/2005 | Shinno et al. |
| 2005/0214171 A1 | 9/2005 | Gerstle et al. |
| 2005/0269214 A1 | 12/2005 | Lee |
| 2005/0277850 A1 | 12/2005 | Mace et al. |
| 2006/0272958 A1 | 12/2006 | Lee et al. |
| 2007/0131548 A1 | 6/2007 | Winarta et al. |
| 2007/0235347 A1 | 10/2007 | Chatelier et al. |
| 2008/0006530 A1 | 1/2008 | Winarta et al. |
| 2008/0128278 A1 | 6/2008 | Bae et al. |
| 2008/0148873 A1 | 6/2008 | Wang |
| 2009/0078030 A1 | 3/2009 | Jung |
| 2009/0157001 A1 | 6/2009 | Jones |
| 2009/0215159 A1 | 8/2009 | Kirby |
| 2011/0048940 A1 | 3/2011 | Wang et al. |
| 2011/0174613 A1 | 7/2011 | Miyazaki et al. |
| 2012/0009095 A1 | 1/2012 | Burke et al. |
| 2012/0055626 A1 | 3/2012 | Bhullar et al. |
| 2012/0174688 A1 | 7/2012 | Calasso et al. |
| 2012/0186996 A1 | 7/2012 | Wilsey et al. |
| 2012/0234487 A1 | 9/2012 | Wang |
| 2013/0027064 A1 | 1/2013 | Austera et al. |
| 2013/0032284 A1 | 2/2013 | Petyt et al. |
| 2013/0062221 A1 | 3/2013 | Cai et al. |
| 2013/0306472 A1 | 11/2013 | Kaneda et al. |
| 2013/0341208 A1 | 12/2013 | Whyte et al. |
| 2014/0021046 A1 | 1/2014 | Huang et al. |
| 2014/0054171 A1 | 2/2014 | Feldman et al. |
| 2014/0147912 A1 | 5/2014 | Cho et al. |
| 2014/0158553 A1 | 6/2014 | Fujiwara et al. |
| 2014/0174922 A1 | 6/2014 | Beer et al. |
| 2014/0262773 A1 | 9/2014 | Riggles et al. |

FOREIGN PATENT DOCUMENTS

| | | |
|---|---|---|
| CN | 99119827.1 | 7/2001 |
| CN | 02111330.0 | 10/2002 |
| CN | 03116172.3 | 10/2003 |
| CN | 03117061.7 | 2/2004 |
| CN | 02139888.7 | 7/2004 |
| CN | 200420091585.4 | 12/2005 |
| CN | 200520017197.6 | 6/2006 |
| CN | 200610088404.6 | 2/2007 |
| CN | 200710178643.5 | 4/2008 |
| CN | 200710040500.8 | 11/2008 |
| JP | 2000162176 | 6/2000 |
| WO | WO 2013117924 | 8/2013 |
| WO | WO 2013190072 | 12/2013 |
| WO | WO 2014140161 | 9/2014 |

OTHER PUBLICATIONS

USPTO Office Action—U.S. Appl. No. 14/099,418, dated Mar. 23, 2016.
USPTO Office Action—U.S. Appl. No. 14/153,654, dated Jun. 14, 2016.
Patent Cooperation Treaty International Search Report—WO2015126456-ISR-010, dated Dec. 22, 2014.
Patent Cooperation Treaty International Search Report—WO2015084448, dated Dec. 22, 2014.
Patent Cooperation Treaty International Search Report—WO2015105536, dated Dec. 22, 2014.

* cited by examiner

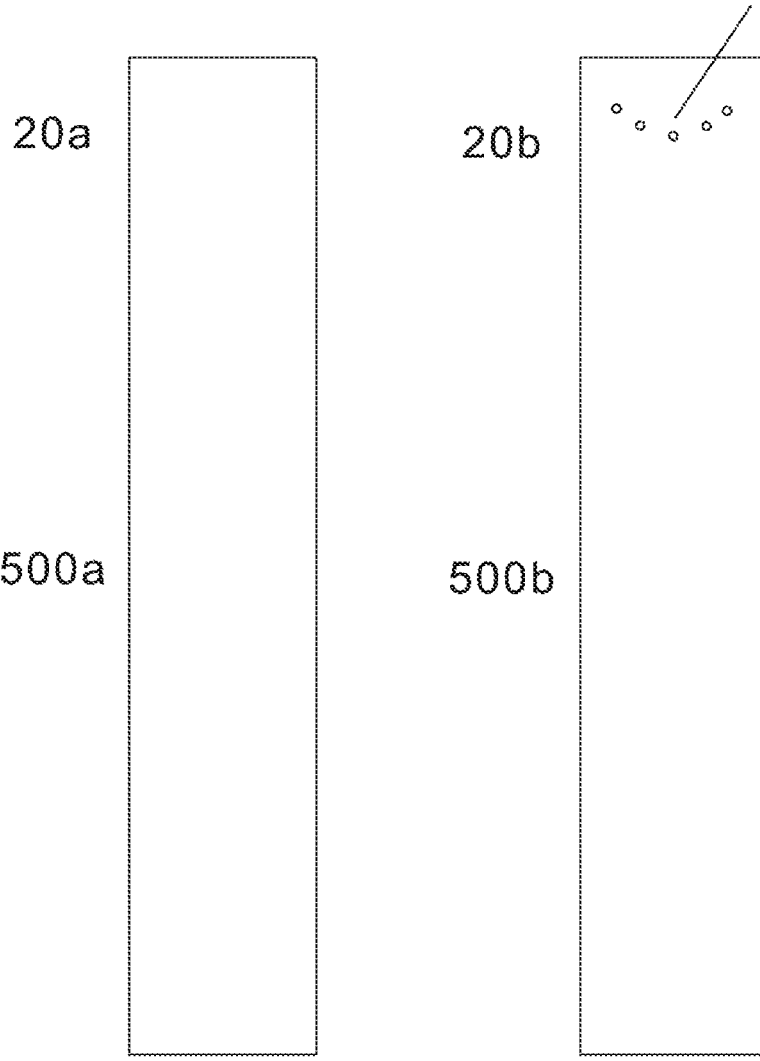

TEST SENSOR WITH MULTIPLE SAMPLING ROUTES

FIELD OF THE INVENTION

The present invention generally relates to a test sensor or strip. More specifically, the present invention generally relates to a disposable biosensor with a thin layer fluid chamber that is adapted to receive a fluid sample with small volume. Still more specifically, the present invention generally relates an electrochemical biosensor with a novel extra wide sampling entrance. Still more specifically, the present invention generally relates an electrochemical biosensor with the fluid chamber with extra wide sampling entrance that can receive a fluid sample from multiple routes. Still more specifically, the present invention relates methods of making and using the biosensors.

BACKGROUND OF THE INVENTION

Electrochemical biosensors or disposable test sensors such as strips are well known and have been used to determine the concentration of various analytes from biological samples, particularly from blood. The accurate determination of analytes in body fluids is of great importance in the diagnoses of certain physiological abnormalities. In particular, it is important that diabetic individuals frequently check their glucose level in their body fluids to regulate the glucose intake in their daily diets. The results of such tests can be used to determine the insulin dosage or other medication needs to be administered. In one type of blood-glucose testing system, test sensors, or called glucose strips, are used by diabetic individuals to test a sample of blood in connection with a hand-held meter. The glucose strips are used by millions of diabetics throughout the world on a daily base.

There are hundreds of brand names of glucose strips in the market. They are very similar in terms of sensor construction: i.e., a channel or chamber is formed between a generally U-shaped spacer and is adapted to receive blood from the opening end of the sensor through capillary action and escape air from the other end through an air escape vent. In order to reduce blood volume, thus reduce pain from piercing finger or other sampling points, the blood receiving chamber is usually small and, as a result, the sampling entrance is also relatively small. As the volume of fluid chambers in the sensors decreases, it becomes increasingly more difficult to fill the fluid chamber with the sample to be analyzed. It has been observed that users may abuse the test sensor by jamming the tip of the test sensor into the individual's finger, which very probably results in incomplete blood filling, non-continuous filling or wiggling of blood flow. Additionally, in some existing test sensors, it is difficult to position the fluid sample within the channel entrance opening especially for those diabetics who have poor vision and/or trembling hands. Besides, blood samples turn to smear around the tip of fingers or other sampling points. It becomes very difficult to draw such smeared blood into the sensor chamber. Each of these shortcomings may, either individually or when combined with one or more of the other shortcomings, contribute to erroneous measurement readings during analysis and may eventually lead to biased readings, and as a result, wrong dosage of insulin administration and even life threatening errors may occur.

Therefore, in order to reduce or eliminate such biased readings caused by such user action and/or reduce the difficulty in connection with sampling, it would be highly desirable to have a more user friendly test sensor that could easily target sample, easily draw sample into the fluid chamber, and alleviate incomplete filling, non-continuous filling and other issues that may result in inaccurate test results. The present disclosure is directed to a novel design and method to overcome one or more of the limitations in the prior arts.

SUMMARY OF THE INVENTION

According to the first embodiment, a disposable electrochemical test sensor has a fluid sample chamber having a novel extra wide sampling entrance. Such a design is adapted to improve sampling of fluid samples. The fluid chamber provides a reservoir from which sample fluid can be drawn into the sample receiving chamber through capillary action. In preferred embodiments, the sensor consists of multiple layers which include a first base layer having conductive coatings serving as working and reference electrodes and having a notch at the sampling entrance end to create additional sampling point; a second base layer having at least one cutout to define the electrode areas and load chemistries and having a notch at the sampling entrance end to create additional sampling point; a first upper layer having semi-circular shape cutout serving as spacer and being slightly shorter than other layers at the sampling end allowing openings at the left and right corners in communication with the fluid chamber; and a second upper layer with a hydrophilic surface facing to the chamber and vent openings at the distal end of the chamber. The base and upper layers are attached through adhesives or other ways to bond each other. Note that the two base layers and the second upper layer are aligned at the front end while the first upper layer is not exposed at the front end as it is slightly shorter. As such, the fluid chamber is formed between a portion of the lower layer surface and the upper layer surface at one end of the sensor, while the other end of the sensor having conductive layer exposed serve as electric contacts in connection with a monitor or meter. The novel extra wide sampling entrance provided by the present invention can draw blood into the chamber through any part of the sampling entrance opening, i.e. it can draw blood into the chamber not only from the front of the sampling entrance as usual in convenient sensors, but also from the bottom, left corner and right corner of the sampling entrance. Thus it allows easily targeting the samples with small volume, picking up smeared samples and alleviating jamming the opening end.

According to the second embodiment, a disposable electrochemical test sensor has a fluid sample chamber having a novel extra wide sampling entrance. Such a design is adapted to improve sampling of fluid samples. The fluid chamber provides a reservoir from which sample fluid can be drawn into the sample receiving chamber through capillary action. In preferred embodiments, the sensor consists of multiple layers which include a base layer having conductive coatings serving as working and reference electrodes and having a notch at the sampling entrance end to create additional sampling point; a second base layer used to define the electrode areas and load chemistries and having a notch at the sampling entrance end to create additional sampling point; a first upper layer having semi-circular shape cutout serving as spacer and being slightly shorter than the base layers and being recessed from a front edge of a upper layer sampling end at the sampling end allowing openings at the left and right corners in communication with the fluid chamber; and a second upper layer with a hydrophilic surface facing to the chamber and vent openings at the distal end of the chamber. The second upper layer is slightly longer than the first upper layer at the sampling end, but slightly shorter than the two base layers, such that the corner opening (both left and right) is created and the surface of the second base layer is partially exposed allowing a top opening once the second upper layer is laminated with other layers. The base and upper layers are attached through adhesives or other ways to bond each other. Note that the two base layers are aligned while the first and second upper layers at the sampling entrance end are not aligned as they are different in length. As such, the fluid chamber is formed between a portion of the lower layer surface and the upper layer surface at one end of the sensor, while the other end of the sensor having conductive layer exposed serve as electric contacts in connection with a monitor or meter. The novel extra wide sampling entrance provided by the present invention can draw blood into the chamber through any part of the sampling entrance opening, i.e. it can draw blood into the chamber not only from the front of the sampling entrance as usual in convenient sensors, but also from the top, bottom, left corner and right corner of the sampling entrance. Thus it allows easily targeting the samples with small volume, picking up smeared samples and alleviating jamming the opening end.

According to one embodiment, a disposable electrochemical test sensor has a sample chamber having a novel extra wide sampling entrance as described in the first and second embodiments, but no additional air escape vent at the second upper layer. Such a design is adapted to improve sampling of fluid samples. The fluid chamber provides a reservoir from which sample fluid can be drawn into the sample receiving chamber through capillary action. The extra wide sampling entrance provided by the present invention can draw blood into the chamber through any part of the opening end. Thus it allows easily targeting the samples with small volume, picking up smeared samples and alleviating jamming the opening end. The extra wide sampling entrance provided by the present invention also serves as the air escape vent. Such one opening sensor eliminates over-flow issue often encountered in convenient sensors.

According to one method, an analyte concentration is measured. A disposable electrochemical test sensor is provided having a sample chamber having a novel extra wide sampling entrance, The chamber provides a reservoir from which sample fluid can be drawn into the sample receiving chamber through capillary action. In preferred embodiments, the sensor consists of laminated multiple layers which include a base layer having conductive coatings serving as working and reference electrodes and having a notch at the sampling entrance end to create additional sampling point and a second base layer used to define the electrode areas and load chemistries and having a notch at the sampling entrance end to create additional sampling point. The notches at the first and second base layers are overlaid to form a notch at the bottom of the fluid chamber. The shape and size and number of the notch are not critical. In one preferred embodiment of the present invention, the notch is a semi-circle in the middle of the front entrance end. The laminated body also includes a first upper layer serves as spacer which may have different shapes, such as circular arc, square, rectangular, triangle, regular trapezoid, inverted trapezoid; and a second upper layer having a hydrophilic surface facing to the chamber with or without vent openings. The upper and base layers are attached through adhesives or other ways to bond each other, such that the fluid chamber is formed between a portion of the lower layer surface and the upper layer surface at one end of the sensor, while the other end of the sensor having conductive layers exposed serve as electric contacts in connection with a monitor or meter.

In one preferred embodiment, the sensor consists of multiple layers which include a base layer having conductive coatings serving as working and reference electrodes and a notch at the sampling entrance end to create additional sampling point; a second base layer having at least one cutout to define the electrode areas and hold chemistries and a notch at the sampling entrance end to create additional sampling point; a first upper layer having semi-circular shape serving as a spacer; and a second upper layer with a hydrophilic surface facing to the chamber and vent openings at distal end of the chamber. The upper and base layers are attached such that the fluid chamber is formed between a portion of the lower layer surface and the upper layer surface at one end of the sensor, while the other end of the sensor having conductive layers exposed serves as electric contacts.

BRIEF DESCRIPTION OF THE DRAWINGS

FIGS. 7a and 7b are top views of the second upper layer without (a) and with (b) vent openings to be used in forming a test sensor according to one embodiment, respectively.

DETAILED DESCRIPTION OF ILLUSTRATED EMBODIMENTS

The test sensor of the present invention is directed to improve sampling entrance of the strip for the determination of an analyte concentration of in a fluid sample, such as blood. In one embodiment, a test sensor is adapted to receive a fluid sample from one end of the sensor, while the other end is connected with an instrument or meter. Analytes that may be measured include, but not limited to glucose, lactate, uric acid, β-hydroxybutyric acid, creatinine, creatine, cholesterol, triglycerides, hemoglobin, bilirubin, alcohol, etc. The fluid sample may be any body fluid, thus, the analytes may be in, for example, a whole blood sample, a blood serum sample, a blood plasma sample, other body fluids like tears, interstitial fluid and urine. In one preferred method, the testing equipment is a hand-held meter.

Figure 1A:
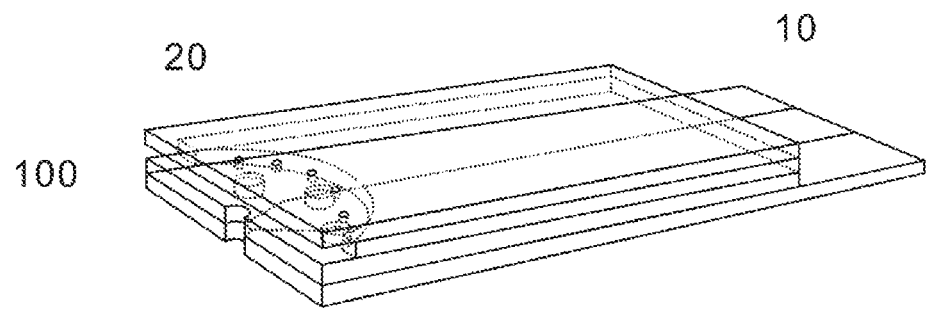
FIG. 1a and FIG. 1b are perspective views of the test sensors of the present invention according to the first embodiment and the second embodiment, respectively.
Figure 1B:
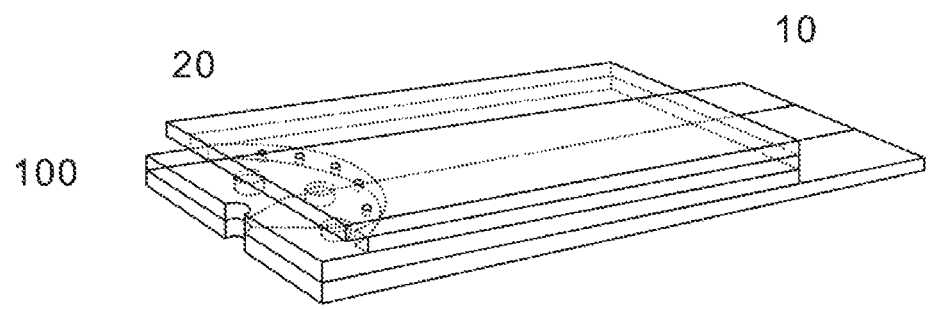

In one embodiment, the test sensor is an electrochemical test sensor. FIG. 1a and FIG. 1b are perspective views of the test sensors of the present invention according to the first embodiment and the second embodiment, respectively. The sensor has a sensor body 100, an electric contact end 10 and sampling end 20. The electric contact end may have at least two contacts used for one working electrode and one reference electrode, respectively. In one preferred embodiment, the electric contact end has three electric contacts serving as contacts for a first working electrode; a second working electrode and a reference electrode, respectively.

Figure 2:
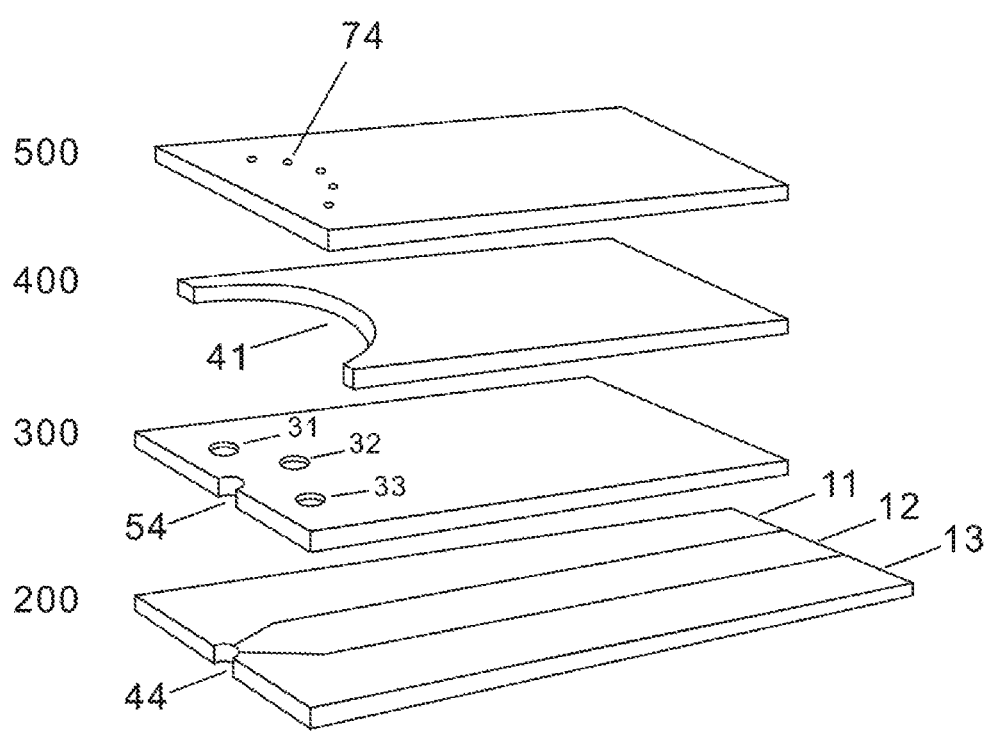
FIG. 2 is an exploded view of the test sensor of the present invention showing the four component layers according one embodiment.

In one embodiment, the test sensor consists of multiple layers which include a first base layer 200; a second base layer 300; a first upper layer 400; and a second upper layer 500, as shown in FIG. 2. The first base layer 200 made of insulating material has conductive coating on the surface. The conductive surface is separated into three conduits. The separate conductive conduits terminate and are exposed for making an electric connection to a reading device at the end 10 opposite the sampling end 20 of the laminated body. The first base layer 200 also has a notch 44 at the front end of the sampling end 20. The second base layer 300 is made of insulating material having three cutouts 31, 32, 33 at the sampling end 20 and a notch 54 at the front end of the sampling end 20. The first upper layer 400 is also made of insulating material and has a semi-circular shaped cutout 41 at the sampling end 20. The second upper layer 500 is still made of insulating material and has several small openings 74 at the sampling end 20. The second upper layer 500 has one side coated with hydrophilic layer which faces the fluid chamber.

Figure 3:
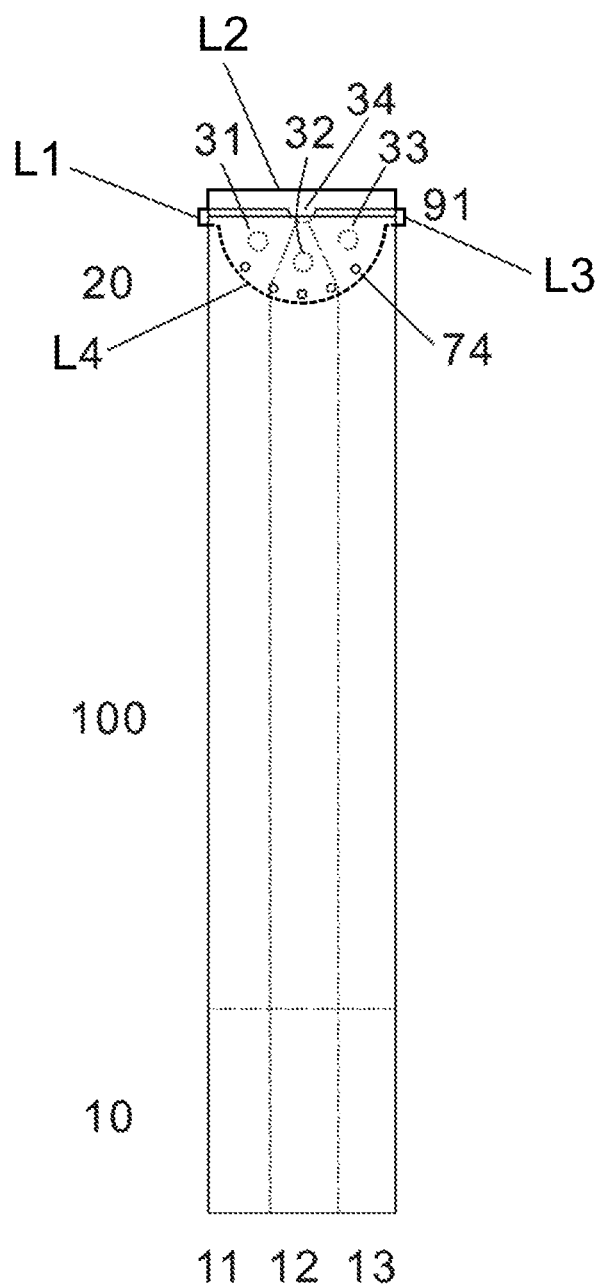
FIG. 3 is a top view of the test sensor of the present invention consisting of four laminated layers according to one embodiment.

FIG. 3 shows a top view of the test sensor consisting of four laminated layers according to one embodiment. The notch 34 is combination of the notch 44 of the first base layer 200 and the notch 54 of the second base layer 300 when they are overlaid. 91 denotes the side opening when all the layers are laminated. As can be seen in FIG. 3, in this embodiment, the opening has a combined length equal to the open front length L2 (which is the same as the width of the test sensor) and the two side opening lengths L1, L3. A perimeter length L4 (which is the bold broken line) of the middle layer front edge which defines the cutout region, and in turn a perimeter of the fluid chamber, is defined as a length of the perimeter edge defined by the cutout from one widthwise end of the middle layer to the other widthwise end. In the embodiment shown, the perimeter length L4 is the length of the semi-circular shaped cutout. The combined length of the opening (L1+L2+L3) is less than the perimeter length L4 of the middle layer cutout region 41b.

Figure 4:
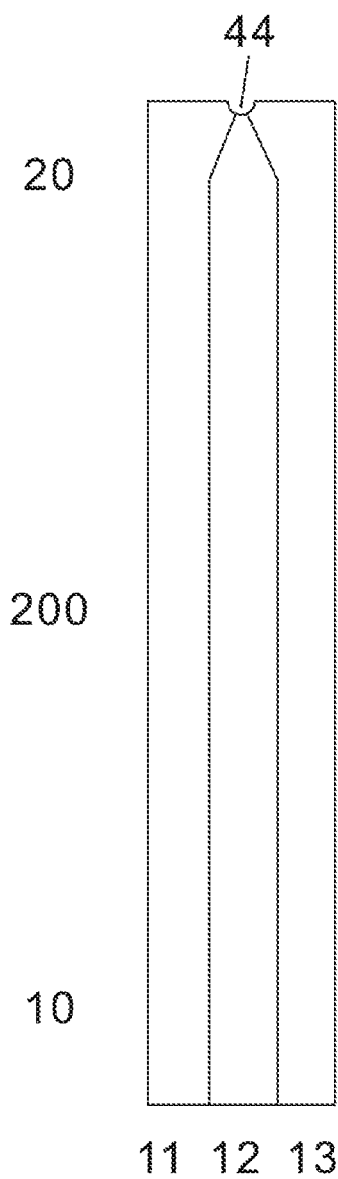
FIG. 4 is a top view of a first base layer to be used in forming a test sensor according to one embodiment.

FIG. 4 shows a top view of a first base layer 200 to be used in forming a test sensor according to one embodiment. The first base layer 200 has three electric conduits for three electrodes at the sampling end 20 and corresponding electric contacts at the electric contact end 10. It also has a notch 44 in the middle of the sampling entrance end. The first base layer 200 may be made from a variety of insulating materials such as polymeric materials, coated with conductive materials such as carbon, various metals or metal oxides. The first base layer 200 with conductive coating serves as substrate of the test sensor. It also serves as electrodes at one end 20 and electric contacts at the other end 10. The insulating layers of the laminated body may be made from any dielectric material. The preferred material is a plastic material. Non-limiting examples of polymeric materials, that may be used to form the base layer include, but not limited to polyethylene, polypropylene, polystyrene, polyvinyl chloride, and polytetrafluoroethylene, polycarbonate, polyethylene terephthalate, polyethylene naphthalate, polyimide and combinations thereof. The conductive coating may be formed by a variety of methods which are well known in the field including, but not limited to printing (e.g., screen-printing), coating (e.g., reverse roll), vapor deposition, sputtering, chemical deposition, and electrochemical deposition. The conductive coating may be on a whole piece of insulating material. If so, a desired number of electric conduits must be made. This can be achieved by etching/scribing the required number of conductive conduits. The etching process may be accomplished chemically, by mechanically scribing lines in the conductive layer, or by using a laser to scribe the conductive layer into separate conductive conduits. The conductive materials may be, but not limited to various carbon materials; various noble metals like gold, platinum, palladium, iridium, rhodium, ruthenium; various metal oxides like indium oxide, tin oxide; and combinations thereof.

Although FIG. 4 shows one notch 44 in the middle of the sampling entrance end. Additional notches could be added along the sampling entrance end, multiple notches could form a saw-tooth like or serrated end. In one preferred embodiment, one notch with a shape of semi-circle is located in the middle of the sampling entrance end, it will be overlaid with the notch 54 of the second base layer to form a notch 34, thus creating additional sampling point (see below). Size and shape as well as number of the notch are not critical. The notch shape could be, but not limited to, circular arc, square, rectangular, triangle, regular trapezoid, inverted trapezoid. In one preferred embodiment, a shape of semi-circle with a diameter of 0.1 to 2 mm is used. More preferably, the diameter is around 1 mm.

Figure 5:
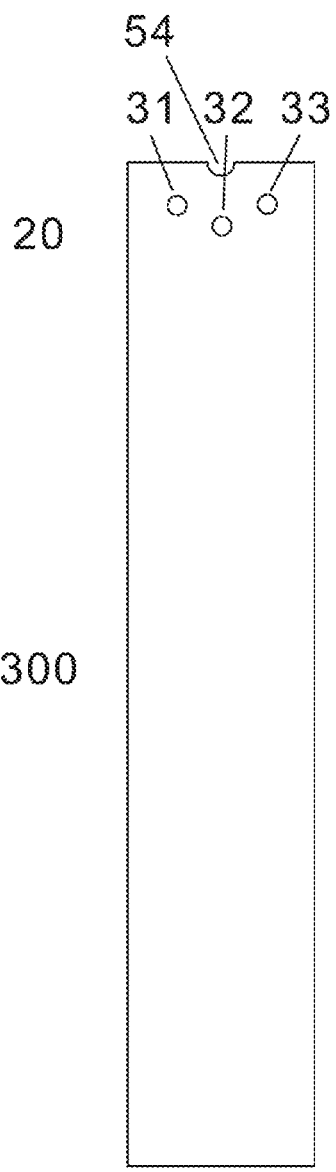
FIG. 5 is a top view of the second base layer to be used in forming a test sensor according to one embodiment.

FIG. 5 shows a top view of the second base layer to be used in forming a test sensor according to one embodiment. The second base layer 300 virtually has same width as the first base layer 200, but shorter in length at the end 10 to expose electric contacts. The second base layer 300 is made of electric insulating layer and it is shorter than the first base layer at the electric contact end 10 so that conductive coating at the first base layer can be exposed for electric contacts when connected with test monitoring device like a hand-held meter. The second base layer 300 has at least one cutout at the end 20. The cutout exposes a part of the conductive layer when laminated with the first base layer 200 and thus defines the electrode area. The cutout can also be loaded with chemistries within the well formed. In one embodiment, the second base layer 300 has at least two such cutouts. In one preferred embodiment, the second base layer 300 has three round cutouts (31, 32, 33) at the end 20 serving as a first working electrode 31; a reference electrode 32 and a second working electrode 33. These cutouts have a diameter ranging from 0.1 mm to 2.5 mm. Preferably, the diameter is ranging from 0.5 mm to 1.5 mm. More preferably, it is around 1 mm. The electrode cutouts 31, 32, 33 have a certain depth, which depends on the thickness of the electric insulating materials used, thus form three wells and can hold chemistries within the wells. Preferably, the thickness of the electric insulating materials is from 0.01 mm to 0.2 mm. More preferably it is around 0.05 mm. In one embodiment of the present invention, the electrode cutouts 31, 32, 33 in the second base layer 300 have the same shape and dimensions. But they can have different shapes, dimensions and/or arrangement orders, without deviating from the scope and spirit of the present invention. The placement of all of the cutouts is such that they will be all positioned within the sample fluid chamber described above. The cutouts may be made by die cutting the insulating material mechanically, or cutting with a laser, and then fastening the material to the first base layer. An adhesive, such as a pressure-sensitive adhesive, may be used to secure the second base insulating layer 300 to the first base layer 200. Adhesion may also be accomplished by ultrasonically bonding the second base layer 300 to the first base layer 200. The second base layer 300 may also be made by screen printing an insulating material, by binding a photopolymer or by heat-sealing an insulating material over the first base layer 200.

The second base layer 300 also has a notch 54 in the middle of the sampling entrance end. Preferably, the notch 54 has the same size, shape and location as the notch 44 at the first base layer 200, such that when all four layers 200, 300, 400 and 500 are laminated as described above figures, the notch 44 at the first base layer and the notch 54 at the second base layer combine and form a notch 34. The notch 34 located at the bottom of the sampling entrance opening, thus, creates an extra opening at the bottom of the sampling entrance, which allows a blood sample entering the fluid chamber through the bottom of the test sensor. This is especially significant for a smeared blood which could be picked up by the bottom sampling point.

Figure 6:
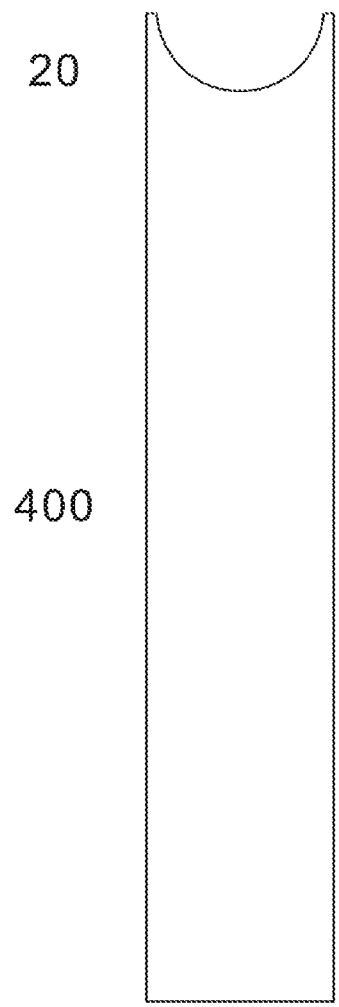
FIG. 6 is a top view of the first upper layer to be used in forming a test sensor according to one embodiment.

FIG. 6 shows a top view of the first upper layer 400 to be used in forming a test sensor according to one embodiment. The first upper layer 400 virtually has same width as the second base layer 300. The first upper layer 400 serves as a spacer in between the two base layers 200/300 and the second upper layer 500. The first upper layer 400, or spacer, is also made of a plastic insulating material with glue or adhesive on both sides and creates the sample fluid chamber of the laminated body. It contains a semi-circular shaped cutout 41 at the sampling end 20 which overlays the second base layer 300 with the open end corresponding to the open end of the laminated body described earlier. The semi-circular shaped cutout 41 has a diameter of at least 1 mm. The diameter of the semi-circle can be larger than or equal to the width of the first base layer 200 or second base layer 300. Preferably, it is slightly smaller than the width of the second base layer 300. More preferably, it is around 2 mm to 20 mm in the present invention. Assuming the test sensor or the component layers (200, 300, 400 and 500) in the present invention have a width of around 6 mm, preferably, the diameter of the semi-circular shaped cutout is around 5.2 mm. A double coated, pressure-sensitive adhesive tape may be used as the first upper layer 400. The cutout 41 creating the fluid chamber may have different shapes and size, without deviating from the scope and spirit of the present invention. The shape may include, but not limited to semi-circular, circular arc, square, rectangular, triangle, regular trapezoid, inverted trapezoid and etc. In one preferred embodiment, the cutout is in semi-circular shape. The thickness and size of the cutout 41 determine the volume of the capillary chamber. Preferably, the first upper layer 400 has a thickness ranging from 0.01 mm to 0.5 mm, thus, the volume of the fluid chamber is about 0.1 to 5 microliter in the present invention. The fluid chamber formed as such allows a blood sample entering the fluid chamber from any part of the entire front opening end. Besides, the first upper layer 400 is shorter in length at the sampling end 20 compared to the base layers 200 and 300, as well as the second top layer 500. As a result, the two base layers and the second upper layer are aligned at the front end of the sampling end 20, while the first upper layer is not exposed, thus leaving side openings 91 at the left corner and right corner in communication with the fluid chamber. Therefore, the sampling entrance extends from the front opening and bottom opening to the side openings, forming an over 180 degree extra wide opening. A blood sample can enter the fluid chamber from any part of the 180 degree extra wide opening.

The laminated body may also have a second upper layer 500a or 500b, bonded to the first upper layer 400. FIGS. 7a and 7b are top views of the second upper layer without (a) and with (b) vent openings to be used in forming a test sensor according to one embodiment, respectively. The second upper layer 500b is alternative to the second upper layer 500a.

According to the first embodiment, the second upper layer 500a or 500b virtually has the same width and length as the second base layer 300. The laminated body is shown in FIG. 1a (using 500b as the second upper layer). The second upper layer 500a or 500b is made of a plastic or polymer materials. Non-limiting examples of polymeric materials, that may be used to form the second upper layer 500a or 500b, include, but not limited to polyethylene, polyethylene terephthalate, polyethylene naphthalate, polyimide and combinations thereof. In one embodiment, the second upper layer 500a or 500b has a hydrophilic surface facing to the chamber to facilitate the capillary action. It should be understood that the entire side of the second upper layer 500a or 500b may be coated with a hydrophilic substance and then bonded to the first upper layer 400.

In case of using 500a as the second upper layer, there are no additional vent openings. Because of the unique design of the extra wide sampling entrance in the present invention, air escape is not an issue when a fluid sample such as blood enter the fluid chamber. Air can always find a way to escape from some part of the wide opening. Therefore, the test sensor of the present invention combines the sampling entrance and air escape vent in one extra wide opening. In case of using 500b as the second upper layer, there are several small vent openings located at the distal end of the chamber. The multiple small vent openings function as air escape vents when a blood sample enters the fluid chamber. It has been found out that multiple small vent openings instead of a large vent opening can effectively eliminates over-flow issues often encountered in conventional sensors. In one preferred embodiment, there are at least two small round vent openings located along the distal end of the fluid chamber. Preferably, the diameter of the openings is less than 0.5 mm. More preferably, it is around 0.1 mm. The test sensor of the present invention has five identical round vent openings located along the distal end of the fluid chamber.

According to the second embodiment, the second upper layer 500a or 500b virtually has the same width as the second base layer 300, but shorter in length, leaving the second base layer 300 partially exposed at the sampling end 20, and thus creating additional top opening at the front of the sampling entrance. The laminated body is shown in FIG. 1b (using 500b as the second upper layer). It can be seen that the sampling entrance is further widen compared to the first embodiment, which may allow a blood sample to enter the fluid chamber from the top of the sampling entrance. To facilitate a sampling from the top, it would be desirable to coat the entire second base layer 300 or at least exposed area with a hydrophilic layer. In one preferred embodiment, it would be desirable to partially or entirely coat the second base layer 300 with a hydrophilic layer. More preferably, it would be desirable to merely coat the exposed part of the second base layer 300 with a hydrophilic layer.

Figure 8A:
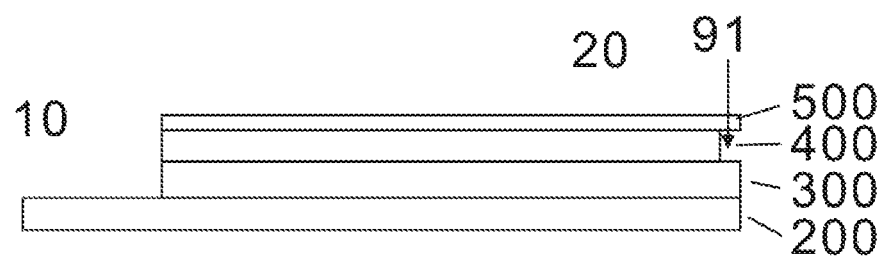
FIGS. 8a and 8b are side views of the test sensors according to the first embodiment (a) and second embodiment (b) of the present invention, respectively.
Figure 8B:
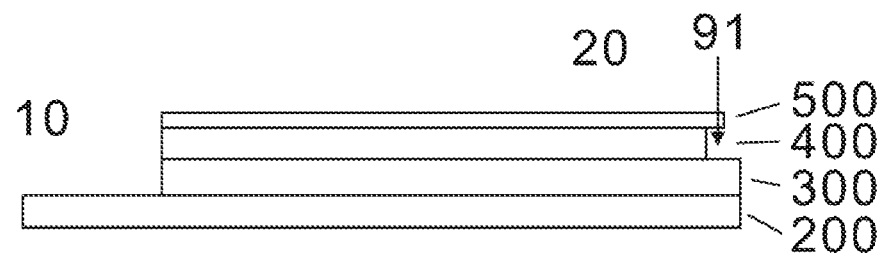

FIGS. 8*a* and 8*b* are side views of the test sensors consisting of four laminated layers including a first base layer 200, second base layer 300, first upper layer 400 and second upper layer 500 according to the first embodiment (FIG. 8*a*) and second embodiment (FIG. 8*b*) of the present invention, respectively. It should be pointed that the second upper layer 500 is aligned with the two base layers 200 and 300 at the sampling end 20 for the first embodiment of the present invention, while it is recessed slightly from the two base layers 200 and 300 for the second embodiment, thus forming a top opening in the second embodiment. 91 denotes the side opening of the laminated body as described earlier. The length of the side opening 91 is preferably from 0.01 mm to 2.5 mm. More preferably, it is from 0.1 to 0.3 mm. Still more preferably, it is around 0.25 mm. It should be emphasized that the side opening 91 in the unique design of the present invention is just a part of the extra wide sampling opening.

In the first embodiment, the side and front opening plus bottom opening combine to form extra wide sampling opening and allow a total of four sampling routes including the front, left, right, and bottom of the sampling opening. In the second embodiment, the side and front opening plus bottom and top opening combine to form extra wide sampling opening and thus allow a total of five sampling routes including the front, left, right, top and bottom of the sampling opening. The advantage of the test sensor of such three-dimension sampling entrances for blood sampling can be illustrated through FIGS. 9 and 10.

Figure 9A:
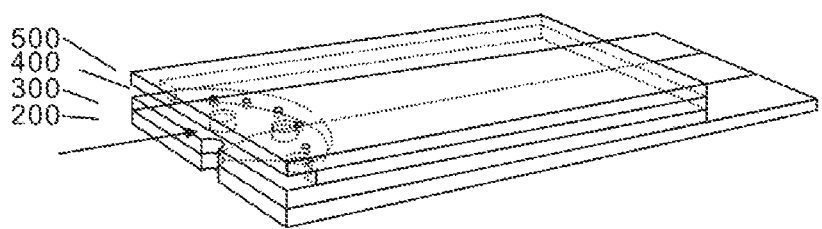
FIGS. 9a, 9b and 9c illustrate that blood can enter the fluid chamber from the front (a), side (b) and bottom (c) of the sampling entrance of the test sensor according to the first embodiment of the present invention, respectively. Note that the test sensor is flipped over in FIG. 9c.
Figure 9B:
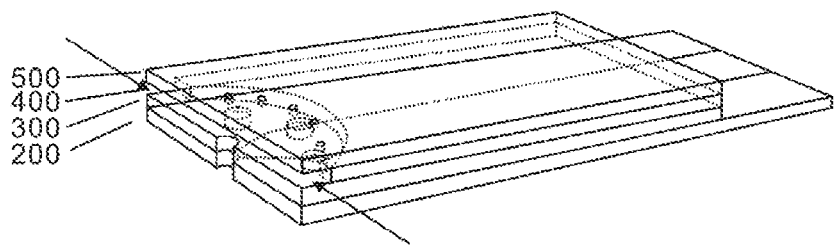
Figure 9C:
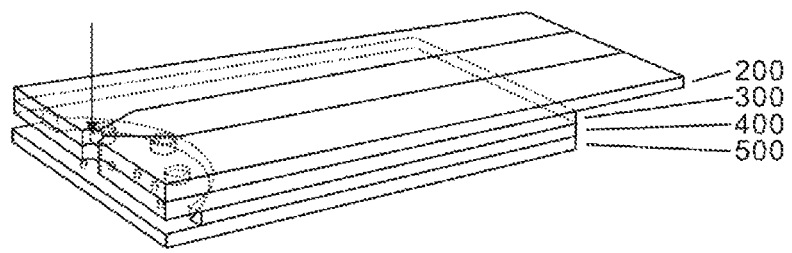

FIGS. 9*a*-9*c* illustrate blood entering the fluid chamber for the test sensor according to the first embodiment of the present invention. Note arrows denote blood sampling directions. Because of the extra wide sampling entrance opening of the present invention, blood sample can enter the fluid chamber from any part of the opening such as, front (FIG. 9*a*); side (left or right, FIG. 9*b*) and bottom (FIG. 9*c*). Also note that the test sensor is flipped over in FIG. 9*c*.

Figure 10A:
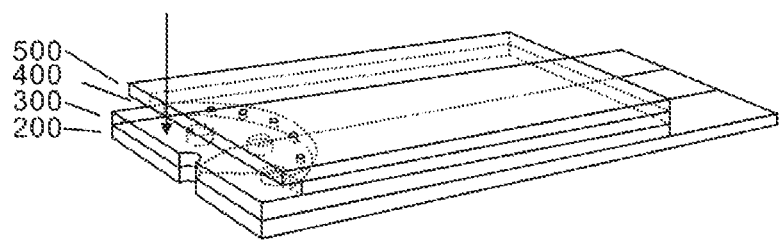
FIGS. 10a, 10b, 10c and 10d illustrate that blood can enter the fluid chamber from the top (a), front (b), side (c) and bottom (d) of the sampling entrance of the test sensor according to the second embodiment of the present invention, respectively. Note that the test sensor is flipped over in FIG. 10d.
Figure 10B:
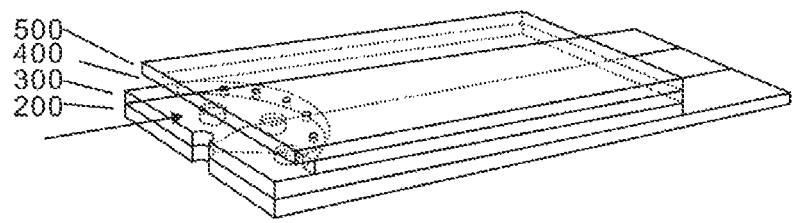
Figure 10C:
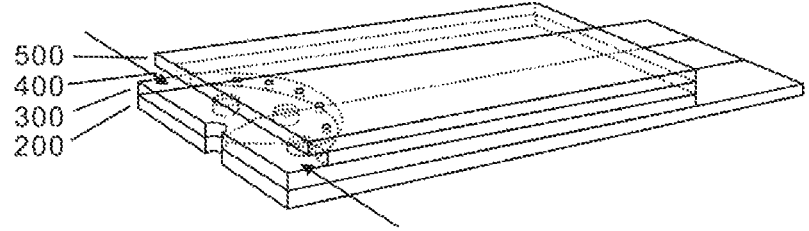
Figure 10D:
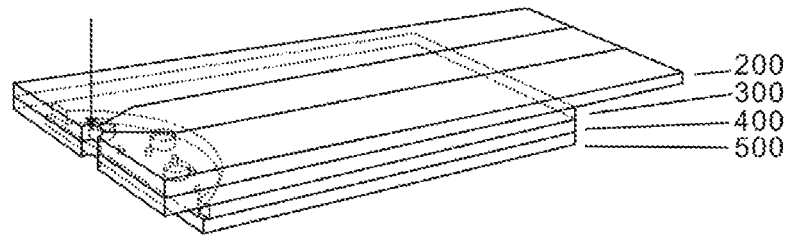

FIGS. 10*a*-10*d* illustrate blood entering the fluid chamber for the test sensor according to the second embodiment of the present invention. Note arrows denote blood sampling directions. Because of the extra wide sampling entrance opening of the present invention, blood sample can enter the fluid chamber from any part of the opening such as, top (FIG. 10*a*); front (FIG. 10*b*); side (left or right, FIG. 10*c*) and bottom (FIG. 10*d*). Note that the test sensor is flipped over in FIG. 10*d*.

By having a test sensor with the extra wide openings in the first embodiment or second embodiment, being adapted to receive a fluid sample, the test sensor of the present invention more easily receives the fluid sample from a user and is more tolerant to users who jam the tip of the sensor into his/her finger, is more tolerant to fluid samples with very small volume (less than 1 microliter) and even smeared samples on the finger tip or other sampling site.

Referring back to FIGS. 1-3, the electrode cutouts 31, 32, 33 may be loaded with chemistries that react with an analyte to produce detectable electrochemical signals. The chemistries may contain an enzyme, an antibody, an antigen, a complexing reagent, a substrate or combination thereof. The reagents are selected to react with the desired analyte or analytes to be tested so as to assist in determining an analyte concentration of a fluid sample. In one embodiment, the reagents typically contain an enzyme such as, for example, glucose oxidase, glucose dehydrogenase, cholesterol oxidase, creatinine amidinohydrolase, lactate oxidase, peroxidase, uricase, xanthine oxidase and etc. which reacts with the analyte and with an electron acceptor such as a ferricyanide salt to produce an electrochemically measurable species that can be detected by the electrodes. For example, if the analyte of the test sensor is glucose, then glucose oxidase or glucose dehydrogenase may be included as the enzyme; if the analyte of the test sensor is uric acid, then uricase may be included as the enzyme. It should be noted that in some cases more than one enzyme may be included to construct the test sensor in order to generate detectable electrochemical signal. For example, in order to make a test sensor for cholesterol, cholesterol esterase, cholesterol oxidase and peroxidase may be included in the sensor.

In order for the test sensor to work effectively, the electrode cutouts 31, 32, 33 may comprise a mixture of a polymer, an enzyme, a surfactant, an electron acceptor, an electron donor, a buffer, a stabilizer and a binder. The electrode cutouts 31, 32, 33 may further include a mediator that is an electron acceptor and assists in generating a current that corresponds to the analyte concentration. The preferable mediators could be redox chemicals either in oxidized or reduced form. The mediator used in the present invention may include, but not limited to various metal or noble metal complexes such as potassium ferricyanide, potassium ferrocyanide, cobalt phthalocyanine, various ferrocenes, and various organic redox mediators such as methylene blue, methylene green, 7,7,8,8-tetracyanoquinodimethane, tetrathiafulvalene, toluidine blue, meldola blue, N-methylphenazine methosulfate, phenyldiamines, 3,3',5,5'-tetramethylbenzidine, pyrogallol, and benzoquinone, phenanthroline-5,6-dione and etc. For example, if the enzyme used to construct the test sensor is glucose oxidase or glucose dehydrogenase, then potassium ferricyanide may be included as redox mediator; if the enzyme used to construct the test sensor includes peroxidase, then potassium ferrocyanide may be included as redox mediator.

The electrode cutouts 31, 32, 33 include a first working electrode 31, a second working electrode 33 and a reference electrode 32. In one embodiment, the second working electrode 33 serves as a blank electrode without loading a chemistry that reacts with the analyte, such that a background signal can be measured and be subtracted from the analyte signal resulted from the first working electrode 31. In this embodiment, effect of interference substances on the analyte signal could be minimized. Still in this embodiment, the electric signals such as current, impedance at the working electrodes 31 and 33, and time to obtain these signals could be used to estimate filling status of the fluid chamber (filled or not). Thus, this embodiment could alert under-fill of fluid samples.

Although the description of test sensor construction above describes construction for a single sensor, the design and materials used can also be used for making multiple sensors from one large piece of each layer material. This would be accomplished by starting with relative large pieces of the first base layer material, second base material, first upper layer material and second upper layer material. After a series of preparations described above, a plurality of multiple test sensors thus can be constructed to achieve mass production in a cost-effective way.

It should be noted that although the particular embodiments of the present invention have been described herein, the above description is merely for illustration purpose. Further modification and variations of the invention herein disclosed will occur to those skilled in the respective arts and all such modifications and variations are deemed to be within the scope of the invention as defined by the appended claims.

What is claimed is:

1. An electrochemical test sensor comprising:
   a continuous base layer having a sampling end and an electric contact end, the base layer having electrodes at the sampling end, and electric contacts at the electric contact end, the electrodes being in communication with the electric contacts;
   a middle layer formed of an electrically insulating material having a width approximately equal to a width of the base layer, and having a sampling end and an electric contact end, the middle layer disposed above the base layer, the middle layer forming a cutout region defined by at least a portion of a front edge being recessed from the middle layer sampling end along the width of the middle layer;
   an upper layer having a sampling end and an electric contact end, the upper layer being attached to the middle layer such that the electric contact end is approximately aligned with the electric contact end of the middle layer, the sampling end of the upper layer being slightly recessed from the sampling end of the base layer, and extending beyond the recessed front edge of the middle layer;
   a single fluid chamber defined on a top by the upper layer, on a bottom by the base layer, on a side by the recessed edge of the middle layer defining the cutout region, and having a sampling entrance defined by an open front opposite to the recessed edge of the middle layer, the fluid chamber sized and configured to receive a fluid by capillary action, and sized and configured to expose the electrodes of the base layer to the fluid;
   wherein the recessed upper layer forms a top opening in communication with the fluid chamber;
   wherein the base layer further defines a recessed notch along its height on the sampling end, the recessed notch creating a bottom opening, the notch and bottom opening providing a fluid communication with the fluid chamber from a front edge and a bottom surface of the electrochemical test sensor, the recessed notch sized and configured to provide the fluid communication via capillary action, and positioned below an area defined by the single fluid chamber so as to directly communicate with the single fluid chamber, wherein the bottom opening is configured to allow a fluid to enter the fluid chamber when the bottom surface of the electrochemical test sensor is parallel to a surface that the fluid is on; and
   wherein the sampling end of the middle layer is recessed from a front edge of the upper layer sampling end and recessed from a front edge of the base layer sampling end, wherein the upper layer, middle layer, and base layer define two side openings in communication with the fluid chamber, each of the two side openings extending from the front edge corners of the sensor;
   the fluid chamber having the sampling entrance to the fluid chamber defined by the open front opposite to the recessed edge of the middle layer, defined by the recessed notch of the base layer, and also defined by the two side openings wherein a combined length of the open front and the two side openings of the fluid chamber is less than a perimeter length of the middle layer front edge.

2. The electrochemical test sensor of claim 1 wherein the base is formed of two parts, a first base layer comprising the electrodes and electric contacts, and a second base layer covering a majority of the first base layer, the second part defining an cutout over each electrode, each cutout in communication with the fluid chamber, each cutout comprising a chemistry configured to react with a fluid when the fluid is within the fluid chamber.

3. The electrochemical test sensor of claim 2 wherein at least one of the chemistries is configured to measure a glucose concentration of the fluid when the fluid is within of the fluid chamber.

4. The electrochemical test sensor of claim 1 wherein the upper layer further defining a plurality of small vent openings, each of the plurality of small vent openings being sized to allow a passage of air, but small enough to prevent a passage of a bodily fluid and wherein each of the plurality of small vent holes has a diameter of approximately 0.1 mm.

5. The electrochemical test sensor of claim 1 wherein the cutout region of the middle layer is formed as a semicircle.

6. The electrochemical test sensor of claim 1 wherein the cutout region of the middle layer extends across a width of the middle layer.

7. The electrochemical test sensor of claim 1 wherein the upper layer further comprises a hydrophilic material on a surface facing the fluid chamber.

8. The electrochemical test sensor of claim 1 wherein the two side openings are configured to allow the fluid to enter the fluid chamber through one of the two side openings when the first or second side is parallel to a surface that the fluid is on.

9. An electrochemical test sensor comprising:
   a continuous base layer having a sampling end and an electric contact end, the base layer having electrodes at the sampling end, and electric contacts at the electric contact end, the electrodes being in communication with the electric contacts;
   a middle layer formed of an electrically insulating material having a width approximately equal to a width of the base layer, and having a sampling end and an electric contact end, the middle layer being disposed above the base layer, the middle layer forming a cutout region defined by at least a portion of a front edge being recessed from the middle layer sampling end along the width of the middle layer;
   an upper layer having a sampling end and an electric contact end, the upper layer being attached to the middle layer such that the electric contact end is approximately aligned with the electric contact end of the base layer;
   a single fluid chamber defined on a top by the upper layer, on a bottom by the base layer, on a side by the recessed edge of the middle layer defining the cutout region, and having a sampling entrance defined by an open front opposite to the recessed edge of the middle layer, the fluid chamber sized and configured to receive a fluid by capillary action, and sized and configured to expose the electrodes of the base layer to the fluid; and
   wherein the base layer further defines a recessed notch along its height on the sampling end, the recessed notch creating a bottom opening at a front bottom edge of the test sensor, the notch and bottom opening providing a fluid communication with the fluid chamber from a front edge and a bottom surface of the electrochemical test sensor, the recessed notch sized and configured to provide the fluid communication via capillary action, and positioned below an area defined by the single fluid chamber so as to directly communicate with the single fluid chamber, wherein the bottom opening is configured to allow a fluid to enter the fluid chamber when the bottom surface of the electrochemical test sensor is parallel to a surface that the fluid is on; and wherein the sampling end of the middle layer is recessed from a front edge of the upper layer sampling end and recessed from a front edge of the base layer sampling end, wherein the upper layer, middle layer, and base layer define two side openings in communication with the fluid chamber, the two side openings being defined by the middle layer sampling end being recessed from the front edge of the upper layer and base layer sampling ends, wherein a combined length of the open front and the two side openings of the fluid chamber is less than a perimeter length of the middle layer front edge.

10. The electrochemical test sensor of claim 9 wherein the base is formed of two parts, a first base layer comprising the electrodes and electric contacts, and a second base layer covering a majority of the first base layer, the second part defining an cutout over each electrode, each cutout in communication with the fluid chamber, each cutout comprising a chemistry configured to react with a fluid when the fluid is within the fluid chamber.

11. The electrochemical test sensor of claim 9 wherein the cutout region of the middle layer is formed as a semicircle.

12. The electrochemical test sensor of claim 9 wherein the cutout region of the middle layer extends across a width of the middle layer.

13. The electrochemical test sensor of claim 9 wherein the notch extends through both the first part and the second part of the base, the notch being semicircular.

14. An electrochemical test sensor comprising:
  a continuous base layer having a sampling end and an electric contact end, the base layer being formed of two parts, a first base layer having three electrodes at the sampling end, and three electric contacts at the electric contact end, the electrodes being in communication with the electric contacts, the second base layer covering at least a portion of the first base layer, the second base layer defining a cutout over each electrode;
  a middle layer formed of an electrically insulating material having a width approximately equal to a width of the base layer, and having a sampling end and an electric contact end, the middle layer disposed above to the base layer, the middle layer forming a cutout region defined by at least a portion of a front edge being recessed from the middle layer sampling end along the width of the middle layer, the cutout region being formed as a semicircle, the semicircle having a diameter slightly less than the width of the middle layer;
  an upper layer having a sampling end and an electric contact end, the upper layer being attached to the middle layer such that the electric contact end is approximately aligned with the electric contact end of the middle layer, the sampling end of the upper layer being slightly recessed from the sampling end of the base layer, and extending beyond the recessed front edge of the middle layer;
  a single fluid chamber defined on a top by the upper layer, on a bottom by the base layer, on a side by the recessed edge of the middle layer defining the cutout region, and having a sampling entrance defined by an open front opposite to the recessed edge of the middle layer, the fluid chamber sized and configured to receive a fluid by capillary action, and sized and configured to expose the electrodes of the base layer to the fluid;
  wherein each cutout of the second base layer is in communication with the fluid chamber, each cutout of the second base layer comprising a chemistry configured to react with a fluid when the fluid is within the fluid chamber to indicate an analyte concentration;
  wherein the recessed upper layer forms a top opening in communication with the fluid chamber;
  the upper layer further comprising a hydrophilic material on a surface facing the fluid chamber;
  wherein the base layer further defines a recessed notch extending along its entire height on the sampling end, the recessed notch creating a bottom opening at a front bottom edge of the test sensor, the notch and bottom opening providing a fluid communication with the fluid chamber from a front edge and a bottom surface of the electrochemical test sensor, the recessed notch sized and configured to provide the fluid communication via capillary action, and positioned below an area defined by the single fluid chamber so as to directly communicate with the single fluid chamber, wherein the bottom opening is configured to allow a fluid to enter the fluid chamber when the bottom surface of the electrochemical test sensor is parallel to a surface that the fluid is on;
  wherein the sampling end of the middle layer is recessed from the front edge of the upper layer sampling end and recessed from a front edge of the base layer sampling end, wherein the upper layer, middle layer, and base layer define two side openings in communication with the fluid chamber, the two side openings being defined by the middle layer sampling end being recessed from the front edge of the upper layer and base layer sampling ends; and
  wherein a combined length of the open front and the two side openings of the fluid chamber is less than a perimeter length of the middle layer front edge.

15. A method of taking a blood sample using the electrochemical test sensor of claim 14 comprising the steps of:
  identifying a blood sample to be analyzed;
  directing the sampling end of the electrochemical test sensor layers to be in contact with the identified blood sample;
  receiving, by capillary action, the identified blood sample within the fluid chamber, the identified blood sample being received into the fluid chamber through at least one of the open side of the fluid chamber, the top opening, the notch of the base layer, and the two side openings; and
  venting air out of the fluid chamber.

* * * * *